(12) United States Patent
Raper et al.

(10) Patent No.: US 10,226,422 B2
(45) Date of Patent: Mar. 12, 2019

(54) SKIN ENHANCING BEVERAGE COMPOSITION

(71) Applicant: BOTTLED SCIENCE LIMITED, London (GB)

(72) Inventors: Piers Raper, Richmond (GB); Christiaan Haig, Richmond (GB); Obi Ejifor, London (GB); Richard Raper, Grand Bahama (BS)

(73) Assignee: BOTTLED SCIENCE LIMITED, London (GB)

( * ) Notice: Subject to any disclaimer, the term of this patent is extended or adjusted under 35 U.S.C. 154(b) by 0 days.

(21) Appl. No.: 14/762,297

(22) PCT Filed: Jan. 23, 2014

(86) PCT No.: PCT/GB2014/050179
§ 371 (c)(1),
(2) Date: Jul. 21, 2015

(87) PCT Pub. No.: WO2014/114939
PCT Pub. Date: Jul. 31, 2014

(65) Prior Publication Data
US 2015/0352045 A1 Dec. 10, 2015

(30) Foreign Application Priority Data

Jan. 23, 2013 (GB) .................................. 1301191.1
Nov. 1, 2013 (GB) .................................. 1319355.2

(51) Int. Cl.
| | |
|---|---|
| *A23L 2/52* | (2006.01) |
| *A23L 2/56* | (2006.01) |
| *A23L 2/66* | (2006.01) |
| *A61K 8/02* | (2006.01) |
| *A61K 8/44* | (2006.01) |
| *A61K 8/46* | (2006.01) |
| *A61K 8/65* | (2006.01) |
| *A61K 8/67* | (2006.01) |
| *A61K 8/92* | (2006.01) |
| *A61K 9/00* | (2006.01) |
| *A23L 33/15* | (2016.01) |
| *A23L 33/17* | (2016.01) |
| *A61K 31/10* | (2006.01) |
| *A61K 31/51* | (2006.01) |
| *A61K 36/55* | (2006.01) |
| *A61K 38/39* | (2006.01) |
| *A61K 45/06* | (2006.01) |
| *A61Q 19/00* | (2006.01) |
| *A61Q 19/06* | (2006.01) |
| *A61Q 19/08* | (2006.01) |
| *A61K 31/375* | (2006.01) |

(Continued)

(52) U.S. Cl.
CPC .............. *A61K 9/0095* (2013.01); *A23L 2/52* (2013.01); *A23L 2/56* (2013.01); *A23L 2/66* (2013.01); *A23L 33/15* (2016.08); *A23L 33/17* (2016.08); *A61K 8/02* (2013.01); *A61K 8/44* (2013.01); *A61K 8/46* (2013.01); *A61K 8/65* (2013.01); *A61K 8/673* (2013.01); *A61K 8/675* (2013.01); *A61K 8/676* (2013.01); *A61K 8/922* (2013.01); *A61K 31/10* (2013.01); *A61K 31/197* (2013.01); *A61K 31/198* (2013.01); *A61K 31/375* (2013.01); *A61K 31/4188* (2013.01); *A61K 31/455* (2013.01); *A61K 31/51* (2013.01); *A61K 31/519* (2013.01); *A61K 31/525* (2013.01); *A61K 31/675* (2013.01); *A61K 31/714* (2013.01); *A61K 36/55* (2013.01); *A61K 38/39* (2013.01); *A61K 45/06* (2013.01); *A61Q 19/00* (2013.01); *A61Q 19/06* (2013.01); *A61Q 19/08* (2013.01); *A23V 2002/00* (2013.01); *A61K 2800/5922* (2013.01); *A61K 2800/92* (2013.01)

(58) Field of Classification Search
None
See application file for complete search history.

(56) References Cited

U.S. PATENT DOCUMENTS

| | | | |
|---|---|---|---|
| 4,647,672 | A | 3/1987 | Seib et al. |
| 5,149,829 | A | 9/1992 | Seib et al. |

(Continued)

FOREIGN PATENT DOCUMENTS

| | | |
|---|---|---|
| CN | 1893841 | 1/2007 |
| CN | 101690601 | 4/2010 |

(Continued)

OTHER PUBLICATIONS

Skinade (The Science Behind Skinade Collagen Drinks, Jun. 17, 2010).*

(Continued)

*Primary Examiner* — Jennifer Pitrak McDonald
*Assistant Examiner* — Tara L Martinez
(74) *Attorney, Agent, or Firm* — Fitch, Even, Tabin & Flannery, LLP

(57) ABSTRACT

The invention provides a beverage composition comprising hydrolyzed collagen and vitamin C, or a derivative thereof, which is particularly suitable for improving skin hydration and skin condition. Additional active ingredients may include methyl sulphonyl methane, a vitamin selected from the vitamin B complex, L-lysine, omega-3 and omega-6 fatty acids. The beverage composition is such that it promotes higher absorption and bioavailability of skin-nourishing ingredients. The beverage composition can improve the moisture content of the skin and can prevent fine lines and wrinkles.

1 Claim, 6 Drawing Sheets

(51) Int. Cl.
*A61K 31/198* (2006.01)
*A61K 31/525* (2006.01)
*A61K 31/455* (2006.01)
*A61K 31/197* (2006.01)
*A61K 31/675* (2006.01)
*A61K 31/4188* (2006.01)
*A61K 31/519* (2006.01)
*A61K 31/714* (2006.01)

(56) References Cited

U.S. PATENT DOCUMENTS

| | | |
|---|---|---|
| 5,948,766 A | 9/1999 | Milan et al. |
| 5,962,025 A | 10/1999 | Carbone et al. |
| 6,010,722 A | 1/2000 | Matsumoto et al. |
| 6,894,029 B1 | 5/2005 | Hsieh |
| 7,070,953 B1 | 7/2006 | Bjarnason et al. |
| 9,072,724 B2 | 7/2015 | Hausmanns et al. |
| 2002/0132780 A1 | 9/2002 | Heisey et al. |
| 2002/0183261 A1 | 12/2002 | Takada et al. |
| 2003/0004315 A1 | 1/2003 | Macdonald et al. |
| 2003/0148923 A1 | 8/2003 | Osajima et al. |
| 2004/0087504 A1 | 5/2004 | Osajima et al. |
| 2004/0115306 A1 | 6/2004 | Lopez et al. |
| 2004/0121949 A1 | 6/2004 | Bonanomi et al. |
| 2004/0162231 A1 | 8/2004 | Hagino |
| 2004/0167318 A1 | 8/2004 | Manickavasagam |
| 2005/0101523 A1 | 5/2005 | Lavigne et al. |
| 2005/0196510 A1 | 9/2005 | Walters |
| 2006/0251750 A1* | 11/2006 | Tabor ............ A61K 31/4188 424/757 |
| 2006/0275345 A1 | 12/2006 | Butzengeiger et al. |
| 2007/0116833 A1 | 5/2007 | Prakash et al. |
| 2007/0116835 A1 | 5/2007 | Prakash et al. |
| 2007/0116838 A1 | 5/2007 | Prakash et al. |
| 2007/0142274 A1 | 6/2007 | Berge |
| 2007/0191282 A1 | 8/2007 | Kagawa et al. |
| 2008/0254505 A1 | 10/2008 | Budolfsen et al. |
| 2009/0269419 A1 | 10/2009 | Pierrisnard et al. |
| 2010/0004182 A1 | 1/2010 | Murota et al. |
| 2010/0068342 A1 | 3/2010 | Matsumoto et al. |
| 2010/0303898 A1 | 12/2010 | Lau et al. |
| 2011/0033606 A1 | 2/2011 | Ito et al. |
| 2011/0039767 A1 | 2/2011 | Nieuwenhuizen et al. |
| 2011/0039768 A1 | 2/2011 | Drieu La Rochelle et al. |
| 2011/0077382 A1 | 3/2011 | Tang et al. |
| 2011/0097448 A1 | 4/2011 | Wong et al. |
| 2011/0124570 A1 | 5/2011 | Drieu La Rochelle et al. |
| 2011/0160137 A1 | 6/2011 | Kim et al. |
| 2011/0257087 A1 | 10/2011 | Krul et al. |
| 2012/0040055 A1 | 2/2012 | Ohara et al. |
| 2012/0077747 A1 | 3/2012 | Anguenot et al. |
| 2012/0114570 A1 | 5/2012 | Bakar et al. |
| 2012/0142598 A1 | 6/2012 | Pam |
| 2012/0253014 A1 | 10/2012 | Higuchi et al. |
| 2013/0252899 A1 | 9/2013 | Hausmanns et al. |

FOREIGN PATENT DOCUMENTS

| | | |
|---|---|---|
| CN | 101766308 | 7/2010 |
| CN | 101889704 | 11/2010 |
| CN | 102224953 | 10/2011 |
| CN | 102524770 | 7/2012 |
| EP | 0682873 | 11/1995 |
| EP | 1075836 | 2/2001 |
| EP | 1623718 | 2/2006 |
| EP | 1673986 | 6/2006 |
| EP | 1872668 | 1/2008 |
| EP | 2532252 | 12/2012 |
| EP | 2666467 | 11/2013 |
| JP | H05199855 | 8/1993 |
| JP | 2004238365 | 8/2004 |
| JP | 2008150326 | 7/2008 |
| KR | 20060123670 | 12/2006 |
| KR | 20100127537 | 12/2010 |
| WO | 199425580 | 11/1994 |
| WO | 200201954 | 1/2002 |
| WO | 200236801 | 5/2002 |
| WO | 2005123108 | 12/2005 |
| WO | 2006034826 | 4/2006 |
| WO | 2006115153 | 11/2006 |
| WO | 2008049942 | 5/2008 |
| WO | 2011014925 | 2/2011 |
| WO | 2011080887 | 7/2011 |
| WO | 2011112100 | 9/2011 |
| WO | 2011112101 | 9/2011 |
| WO | 2012035869 | 3/2012 |
| WO | 2012049430 | 4/2012 |
| WO | 2012141795 | 10/2012 |
| WO | 2012147842 | 11/2012 |

OTHER PUBLICATIONS

OSU, Linus Pauling Insititute: Micronutrient Information Center [retrieved on Nov. 21, 2017]. [Retrieved from internet: http://lpi.oregonstate.edu/mic/vitamins/vitamin-C/supplemental-forms]; 2017.*

Orthomolecular.org—Orthomolecular Medicine News Service, Dec. 8, 2009.*

Ley, "MSM: On Our Way Back to Health with Sulfur", Bl Pubns, Jan. 1998.

Fried, "Healting Adult Acne: Your Guide to Clear Skin and Self-Confidence", New Harbinger Publications, Oct. 1, 2005.

Gamwell, "95 Surprisingly Effective Natural Ways to Fight Acne", CreateSpace Independent Publishing Platform, Aug. 31, 2011.

* cited by examiner

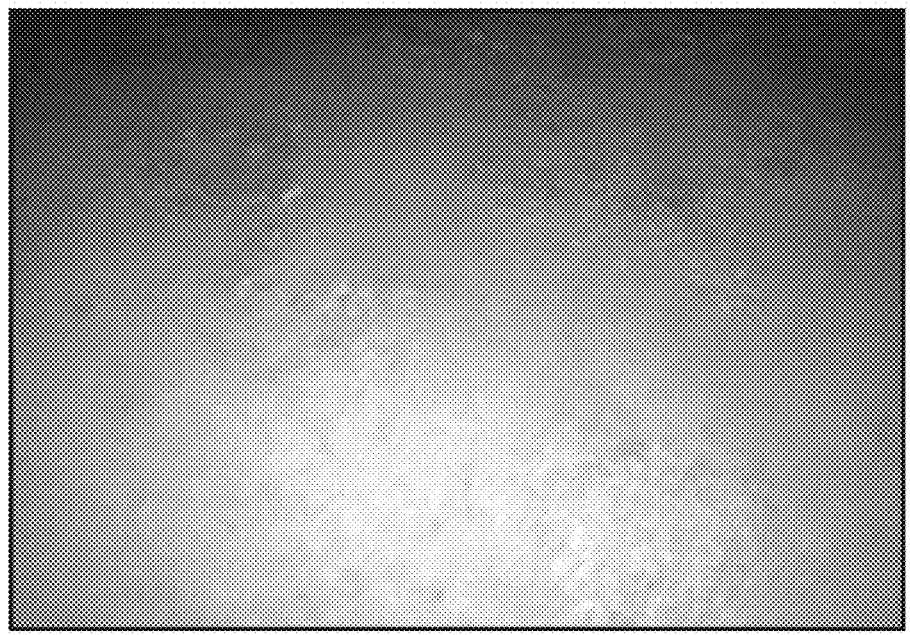

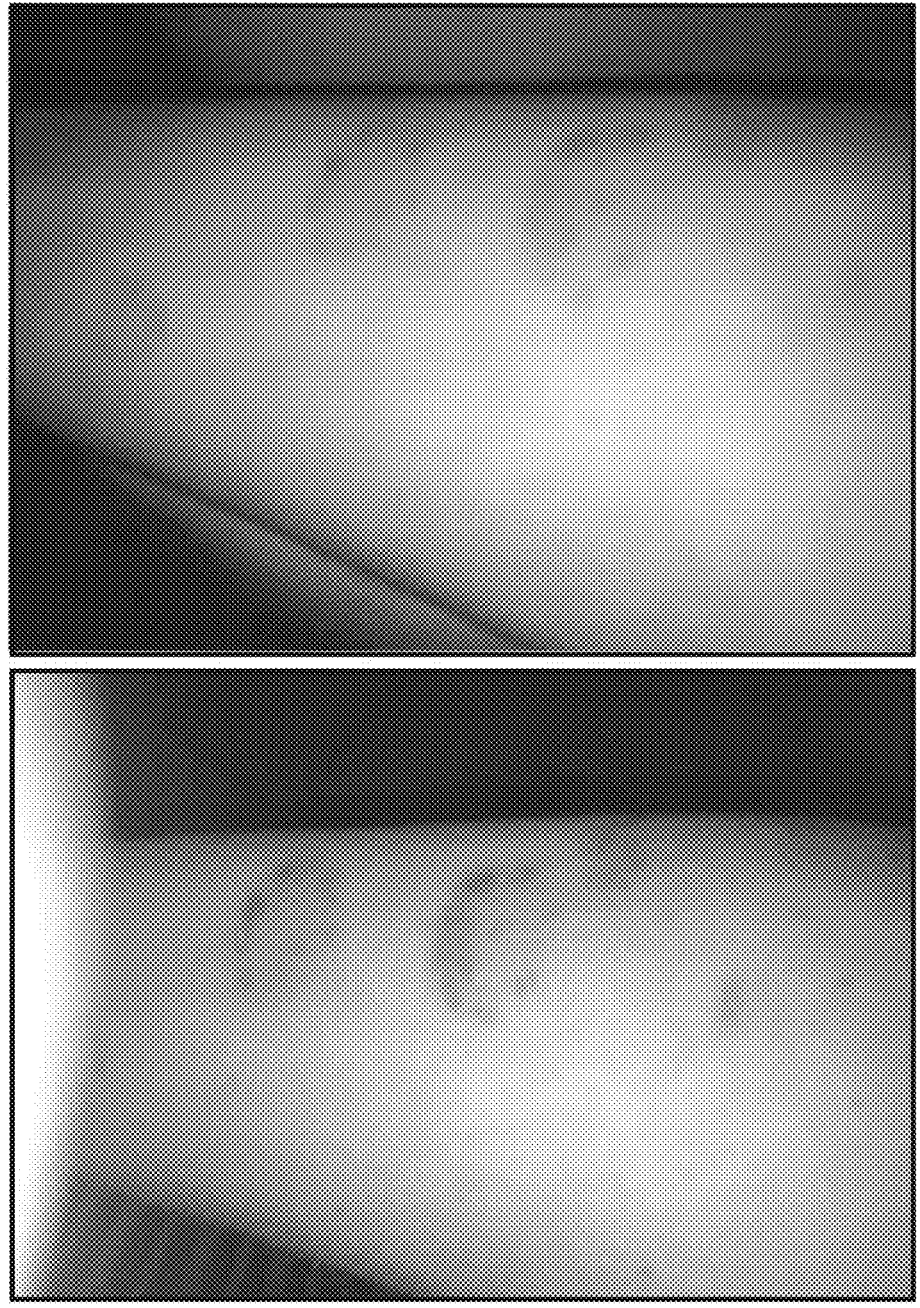

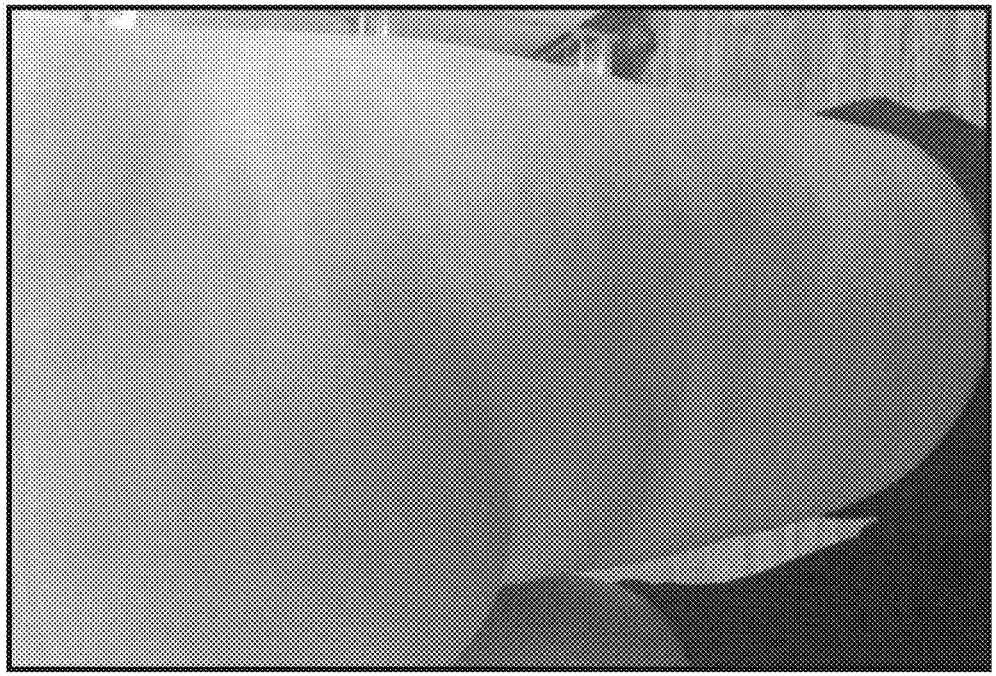

SKIN ENHANCING BEVERAGE COMPOSITION

CROSS REFERENCE TO RELATED APPLICATIONS

The present application is a National Stage Application claiming the priority of co-pending PCT Application No. PCT/GB2014/050179, filed Jan. 23, 2014, which in turn, claims priority from Great Britain application Serial Nos. 1301191.1, filed Jan. 23, 2013 and 1319355.2, filed Nov. 1, 2013. Applicant claims the benefits of 35 U.S.C. § 120 as to the PCT application and priority under 35 U.S.C. § 119 as to the said Great Britain applications, and the entire disclosures of all applications are incorporated herein by reference in their entireties.

FIELD OF THE INVENTION

The present invention relates to a beverage composition that is particularly suitable for improving skin hydration and skin condition and which promotes prevention and amelioration of e.g. fine lines and wrinkles.

BACKGROUND OF THE INVENTION

The skin provides the body with mechanical protection and acts as a chemical barrier to restrict foreign substance penetration, to prevent water or fluid loss and to maintain a constant temperature.

The skin is subject to deterioration due to environmental factors and throughout the normal ageing process. This deterioration can lead to wrinkles, fine lines and dry or thinning skin.

There are many cosmetic methods for improving skin nourishment, hydration and the appearance of the skin. These include topical application of creams and lotions which contain ingredients that improve the skin quality.

The effect of topical application is only local and the benefits are only provided to the part of the skin where the cream or lotion is applied. This is usually on the outer layer of the skin, the epidermis.

Skin creams and lotions may provide a change to the epidermis, but the effects of these creams do not reach the dermis, or inner regenerative layer of the skin.

The systemic administration of ingredients that can improve the skin condition could be beneficial, especially if they could be orally administered and distributed to the whole body and entire thickness of the skin, in particular, the inner regenerative layer.

Some health care and beauty care foods have been developed which enhance the properties of the skin by oral ingestion. For example, foods comprising collagen, vitamins and proteins (CN-A-101766308 and CN-A-101889704), compositions comprising vegetable oils, vitamins and minerals (US-A-2009/0269419), foods comprising hyaluronic acid to promote water retention (EP-A-1075836 A2) and health foods or drinks comprising collagen production promoters such as milk-derived basic protein fractions (EP-A-1623718 A1).

Collagen is a structural protein of the extracellular matrix and it has been shown that skin collagen content declines with age, leading to a loss of the skin elasticity and to the formation of fine lines and wrinkles. CN-A-101766308 describes the use of a collagen liquid drink to enhance the health of human skin. The combination of collagen peptide and vitamins (including vitamin C) can replenish the loss of the body's collagen. EP-A-1623718 describes the use of basic peptide fractions to promote skin collagen level. US 20110160137 discusses the use of an oral composition comprising a collagen peptide, proteins and vitamins which can maximise collagen biosynthesis and improves skin condition.

Vitamin C (ascorbic acid) is known as an acidulent, vitamin, and antioxidant substance. WO-A-0201954 describes the use of L-ascorbyl monophosphate to promote cellular regeneration and repair after injury. U.S. Pat. No. 4,647,672 and U.S. Pat. No. 5,149,829 describe stable, 2-polyphosphorylated species of L-ascorbic acid and its stereoisomers. The 2-polyphosphate esters of L-ascorbate described in these patents have proved to be an excellent source of vitamin C for nutrition, on account of their stability, low solubility and high bioavailability.

EP-A-2532252 describes the combination of collagen, hyaluronic acid, borage oil emulsion and a glucosamine derivative which is said to be particularly suitable for improving skin condition.

The existing skin-enhancing liquid dosage forms suffer from low palatability leading to poor compliance by the subject. Moreover, the performance of these compositions in use has been disappointing. It is thought that this may be due, inter alia, to low bioavailability of the collagen after ingestion.

It would be beneficial to provide a beverage composition that promotes higher absorption and bioavailability of skin-nourishing ingredients.

SUMMARY OF THE INVENTION

The object of this invention is to provide a beverage for improving skin quality, particularly by improving hydration, elasticity and tension of both epidermis and dermis through the synergistic effects exerted by its ingredients and by means of the administration route.

In a first aspect, the present invention provides a beverage composition comprising collagen, and vitamin C, or a derivative thereof, wherein the collagen is present in an amount between about 2 and 10 g/100 ml and the vitamin C, or derivative thereof, is present in an amount between about 50 and 400 mg/100 ml. The weight ratio of collagen to vitamin C is between 10:1 and 50:1. The combination of collagen and vitamin C in this ratio promotes higher absorption and bioavailability of skin-nourishing ingredients. The relatively low ratio of vitamin C to collagen improves palatability of the beverage while providing the above advantages.

Suitably, the beverage composition also comprises at least one further active ingredient, for example selected among methyl sulphonyl methane (MSM), a vitamin such as a vitamin selected from the vitamin B complex, L-lysine, omega-3 and omega-6 fatty acids.

Suitably, the beverage composition comprises at least 75% by weight of water, more suitably at least about 80% of water, and most suitably at least about 90% by weight of water. The high dilution of the compositions also improves palatability and acceptability of the beverage.

Suitably, the beverage composition further comprises one or more ingredients selected from flavouring agents, colourants, sweeteners, fruit juice concentrate and acidulants. The beverage composition can also comprise other ingredients from vitamins, minerals, additives, antioxidants, carbohydrate sources, amino acids and trace elements.

Suitably, the present invention further provides use of a beverage composition of the present invention for improving skin conditioning, skin hydration, skin nourishment and skin appearance. The present invention further provides use of a beverage composition of the present invention for alleviating eczema, psoriasis, acne and/or cellulite. The present invention further provides a beverage composition of the present invention for use in therapy. The present invention further provides a beverage composition of the present invention for use in the treatment of eczema, psoriasis, acne or cellulite. The invention further provides a method of treating eczema, psoriasis, acne or cellulite comprising administration to a patient in need thereof an effective amount of a beverage composition of the present invention.

Eczema includes the following types of eczema: atopic eczema, contact dermatitis, seborrhoeic eczema, discoid eczema, gravitational eczema, asteatotic eczema and pompholyx eczema.

Psoriasis includes the following types of psoriasis: psoriasis vulgaris, guttate psoriasis, inverse psoriasis, pustular psoriasis and erythrodermic psoriasis.

BRIEF DESCRIPTION OF THE DRAWINGS

FIG. 1A shows an area of an individual's skin affected by eczema before consumption of the beverage composition of the present invention. FIG. 1B shows the same area of skin after the individual had been taking the beverage composition of the present invention for 15 days.

FIG. 3A shows an area of an individual's skin affected by psoriasis before consumption of the beverage composition of the present invention. FIG. 3B shows the same area of skin after the individual had been taking the beverage composition of the present invention for 15 days.

FIG. 6A shows an area of an individual's skin affected by cellulite before consumption of the beverage composition of the present invention. FIG. 6B shows the same area of skin after the individual had been taking the beverage composition of the present invention for 15 days.

DETAILED DESCRIPTION OF THE INVENTION

Figure 2A:
FIG. 2A shows an area of an individual's skin affected by psoriasis before consumption of the beverage composition of the present invention.

Hereinafter, the present invention will be described in further detail with reference to suitably preferred embodiments. Any combination of the preferred ingredients and amounts herein may be present in the compositions, and the scope of the invention is not limited to the specific combinations and amounts of ingredients disclosed but only by the scope of the accompanying claims.

The present invention provides a beverage composition comprising collagen and vitamin C, or a derivative thereof, as defined in claim 1.

Collagen is the main structural protein of the skin and provides tensile strength and elasticity to the dermal matrix. It has been shown that skin collagen content declines with age, leading to a loss of skin elasticity and to the formation of fine lines and wrinkles.

The collagen used in the present invention is suitably derived from animal or marine sources. In particular, the collagen is preferably hydrolysed collagen, preferably with a molecular weight of about 500 to 20000 Da. Suitably, the collagen is hydrolysed marine collagen. Suitably, the collagen is able to dissolve and produce a clear solution having low viscosity in water in the claimed concentration range.

The term "Vitamin C" herein refers to ascorbic acid. The vitamin C derivative may be an ascorbate salts, such as a salt with one or more cations from Group IA elements, Group IIA elements, or quaternary ammonium ions. A suitable ascorbate salt is calcium ascorbate, which is available under the name Ester-C® available from The Ester C Company, Bohemia, N.Y., USA. This salt is kinder to the stomach than ascorbic acid. In other embodiments, the vitamin C derivative may be an ester of ascorbic acid, such as an alkyl, alkoxy, or phosphate ester or polyphosphate ester. A suitable ester is ascorbate-2-diphosphate or ascorbate-2-triphosphate or mixtures thereof, for example as available under the Registered Trade Mark STAY-C. In a preferred embodiment, the vitamin C derivative comprises, consists of, or consists essentially of calcium ascorbate.

In the present invention, the beverage composition comprises collagen in an amount between about 2 and 10 g/100 ml, preferably in an amount between about 4 and 6 g/100 ml, and vitamin C, or a derivative thereof, which is present in an amount between about 50 and 400 mg/100 ml, preferably in an amount between about 100 and 300 mg/100 ml, for example between about 150 and about 250 mg/100 ml. (These amounts are for calcium ascorbate, which has a molecular weight of 390.3. For other vitamin C derivatives suitable ranges are those that provide the equivalent molar amounts of ascorbate to these weight ranges of calcium ascorbate).

The weight ratio of collagen to vitamin C (as calcium ascorbate) in the beverage composition is between 10:1 and 50:1, suitably between 20:1 and 40:1.

The present inventors have found that the claimed ratio of collagen to vitamin C provides a synergistic effect and leads to an improvement of skin hydration, elasticity and firmness. To avoid problems such as increased viscosity of the beverage, the collagen content is kept below 10 g/100 ml. The vitamin C, or a derivative thereof, is present in an amount between about 50 and 250 mg/100 ml. Combining collagen with vitamin C, or a derivative thereof, in this ratio promotes higher absorption and bioavailability of skin-nourishing ingredients and thereby increases skin collagen synthesis and can lead to improved skin appearance and condition. Moreover, palatability of the beverage is excellent.

The beverage composition according to the present invention should suitably contain other components which have a beneficial effect on the skin, for example, methyl sulphonyl methane (MSM), vitamins of the vitamin B complex, L-lysine, omega-3 and omega-6 fatty acids.

The methyl sulphonyl methane is a naturally occurring form of organic sulphur and can be present in an amount between about 300 and about 800 mg/100 ml, preferably in an amount between about 500 and about 700 mg/100 ml.

The vitamin B is selected from B1, B2, B3, B5, B6, B7, B9, B12 and mixtures thereof. The vitamin B complex can suitably be present in a total amount of between about 25 and about 100 mg/100 ml, preferably in an amount between about 80 and about 100 mg/100 ml, preferably in an amount between about 85 and about 95 mg/100 ml.

The L-lysine can be present in an amount between about 60 and 100 mg/100 ml, preferably between about 70 and 90 mg/100 ml.

It has been shown that increased skin hydration and nourishment can be achieved using a combination of different omega fatty acids. Preferably, the omega fatty acids are selected from omega-3, omega-6 and mixtures thereof. The omega-3 and omega-6 can be in the form of free fatty acids, fatty acid salts or fatty acid esters, such as oils. The combination of omega-3 and omega-6 provides nourishment of the skin by providing precursors for lipids that improve skin barrier function. They play a vital role in preserving the natural barrier of the skin against water-loss and in the maintenance of the stability of dermal cells. By preventing water-loss, omega-3 and omega-6 fatty acids can prevent dryness of the skin.

The omega-3 and omega-6 fatty acids are suitably derived from fish oils, fungal oils or plant oils. Suitably flax seed oil is used. The total content of omega-3 and omega-6 fatty acids or derivatives thereof can be an amount between about 15 and 50 mg/100 ml, preferably between about 20 and 40 mg/100 ml.

The beverage composition according to the present invention may be provided as a ready-to-drink beverage. Such beverage composition contains a liquid or fluid suitable for diluting the composition of the present invention. Examples of suitable liquids or fluids are water, coffee, tea, juice, milk, milk substitutes, milk products such as yoghurt and/or general flavoured beverages on the basis of water. The amount of water, water-based liquids, milk or mixtures thereof utilised in the present beverage composition comprises at least about 75% to about 95%, more preferably at least about 80% and even more preferably at least about 90% of the total weight of the composition.

Suitably the present invention provides a beverage composition which comprises water as the fluid. The water content of the beverage composition is preferably at least about 75%, more preferably at least about about 80% and even more preferably at least about 90% of the total weight of the composition.

According to further aspects of the present invention, the beverage composition should preferably contain additional components to enhance the beverage composition. For example, one or more ingredients selected from flavouring agents, colourants, sweeteners, fruit juice concentrate and acidulants may be included in the beverage composition.

Suitably, the sweetener comprises sucralose. Further, said sucralose is present in an amount between about 8 and 16 mg/100 ml, preferably between about 10 and 14 mg/100 ml. The use of a sweetener can improve the taste of the beverage composition.

Suitably, the flavouring agent can be used to further improve the taste of the beverage composition. As a flavour, a peach or mangosteen flavour is particularly preferable.

Suitably the present invention provides a beverage composition that could contain additional optional components. For example, the beverage composition may comprise one or more vitamins, minerals, additives, antioxidants, carbohydrate sources, amino acids, trace elements, hyaluronic acid, glucosamine, fruit/vegetable juices, preservatives (such as potassium sorbate), emulsifiers/hydrocolloids, oils, carbonation components and the like may be included in the compositions herein. Such optional components may be dispersed, solubilised or otherwise dispersed into the present beverage compositions.

The beverage composition according to the present invention preferably does not contain hyaluronic acid. Furthermore, the suitable beverage composition preferably does not contain glucosamine. Wither reference to composition, the term "does not contain" means less than 0.1% of the total weight of the composition. In a further embodiment, the suitable beverage composition preferably does not contain green tea extract.

The beverage composition can be suitably packaged as a dose of about 100 to 200 ml, preferably as a dose of about 140 to 160 ml, more preferably as a dose of about 150 ml. Suitably, the beverage composition can be consumed by a human on a once-a-day basis. Suitably, the beverage composition is taken as a 150 ml dose each day.

The beverage composition claimed is of cosmetic value. When the beverage composition of the present invention is orally consumed, it exerts a promoting effect on skin collagen production and skin hydration. The beverage composition can be used to provide skin nourishment and anti-ageing properties to a person in need comprising the step of consuming an effective amount of the beverage composition. As an example, the effective amount can be in the form of a 150 ml dosage of the beverage composition.

Preferably, the beverage composition is given as a 100 to 200 ml daily dose. It has been shown that, after a four week treatment subjects notice improvements in their skin quality. Improvements include increased hydration levels, improved skin elasticity and firmness and the reduced formation of deep wrinkles and fine lines.

The beverage composition of the present invention is primarily applicable in a non-medical cosmetic method. It can be used to provide skin nourishment and reduce the signs of ageing and could be used by individuals who so desire. The beverage composition of the present invention may also be used in a cosmetic method of alleviating eczema, psoriasis, acne and/or cellulite. The beverage composition of the present invention may also be used in a therapeutic method, such as in the treatment of eczema, psoriasis or acne. The beverage composition of the invention is preferably ingested in the form of a 100 to 200 ml daily dose containing the beverage composition.

Table 1 reports the content range of the ingredients that can suitably be combined in the water based beverage composition as described above. The water content of this particular composition is at least about 90% by weight.

| Ingredients | Content range/100 ml |
| --- | --- |
| Collagen | 2-10 g, preferably 4-6 g/100 ml |
| Vitamin C | 100-400 mg, preferably 100-300 mg/100 ml, preferably 150-250 mg/100 ml |
| Methyl sulphonyl methane | 300-800 mg, preferably 500-700 mg/100 ml |
| Vitamin B complex | 25-100 mg, preferably 80-100 mg, preferably 85-95 mg/100 ml |
| L-lysine | 60-100 mg, preferably 70-90 mg/100 ml |
| Omega-3 and omega-6 (as flax seed oil) | 15-50 mg, preferably 20-40 mg/100 ml |

The invention will now be described further with reference to the following specific example.

Example 1

A beverage composition is prepared by combining the following components in a conventional manner. After mixing all the ingredients, the water is added in order to adjust the volume to 100 ml.

| Ingredients | Content/ 100 ml |
| --- | --- |
| Collagen | 4.6 g |
| Vitamin C (calcium ascorbate) | 200 mg |
| Methyl sulphonyl methane | 667 mg |
| Vitamin B complex | 93 mg |
| L-lysine | 80 mg |
| Omega-3 and omega-6 (flax seed oil) | 30 mg |
| Sweetener (Sucralose) | 12 mg |
| Flavourings (peach and mangosteen) | 280 mg |
| Colourant (carrot concentrate and blackcurrant) | 50 mg |
| Grape juice concentrate | 500 mg |
| Acidulant | 200 mg |
| Water | 93.328 g |

Example 2

A beverage composition (in a different volume package) is prepared by combining the following components in a conventional manner. After mixing all the ingredients, the water is added in order to adjust the volume to 150 ml.

| Ingredients | Content/ 150 ml |
| --- | --- |
| Collagen | 6.9 g |
| Vitamin C (calcium ascorbate) | 300 mg |
| Methyl sulphonyl methane | 1.001 g |
| Vitamin B complex | 140 mg |
| L-lysine | 120 mg |
| Omega-3 and omega-6 (flax seed oil) | 45 mg |
| Sweetener (Sucralose) | 18 mg |
| Flavourings (peach and mangosteen) | 420 mg |
| Colourant (carrot concentrate and blackcurrant) | 75 mg |
| Grape juice concentrate | 750 mg |
| Acidulant | 300 mg |
| Water | 139.992 g |

Example 3

A beverage composition is prepared by combining the following components in a conventional manner. After mixing all the ingredients, the water is added in order to adjust the volume to 150 ml.

| Ingredients | Content/ 150 ml |
| --- | --- |
| Collagen | 7.0 g |
| Vitamin C (calcium ascorbate) | 180 mg |
| Methyl sulphonyl methane | 1.0 g |
| Thiamine (vitamin B1) | 4 mg |
| Riboflavin (vitamin B2) | 6 mg |
| Niacinamide (vitamin B3) | 17 mg |
| Pantothenic acid (vitamin B5) | 21 mg |
| Pyridoxine (vitamin B6) | 4 mg |
| Biotin (vitamin B7) | 200 µg |
| Folic acid (vitamin B9) | 200 µg |
| Cobalamin (vitamin B12) | 10 µg |
| L-lysine | 124 mg |
| Omega-3 and omega-6 (flax seed oil) | 45 mg |
| Sweetener (Sucralose) | 18 mg |
| Flavourings (peach and mangosteen) | 420 mg |
| Grape juice concentrate | 750 mg |
| Acidulant (citric acid) | 300 mg |
| Water | 139.992 g |

The beverage compositions as described above were tested on a sample of 10 individuals over a period of four weeks. Beverage intake of 150 ml dosage a day was shown to improve hydration levels and skin smoothness after one week of use, improve the radiance, glow and skin texture after two weeks of use, improve skin elasticity and firmness after three weeks of use and reduce the formation of deep wrinkles and fine lines after four weeks of use. Such intake was also shown to alleviate eczema, psoriasis, acne and cellulite.

Example 4

The beverage composition described in Example 3 was tested on a panel of 62 individuals who took the product and then self-assessed their skin condition based on the questions set out in the table below.

| Question | No. of respondents | Yes Count | Yes % | No Count | No % |
| --- | --- | --- | --- | --- | --- |
| My skin feels more hydrated | 62 | 60 | 97% | 2 | 3% |
| My skin looks more radiant | 61 | 51 | 84% | 10 | 16% |
| My skin looks clearer | 61 | 54 | 89% | 7 | 11% |
| My skin looks healthier | 60 | 57 | 95% | 3 | 5% |
| My skin has better elasticity | 60 | 47 | 78% | 13 | 22% |
| My skin feels smoother | 61 | 53 | 87% | 8 | 13% |
| My skin looks younger | 59 | 40 | 68% | 19 | 32% |
| My skin is better | 60 | 57 | 95% | 3 | 5% |
| I have fewer fine lines or wrinkles | 57 | 34 | 60% | 23 | 40% |
| I have started to receive compliments about my skin | 59 | 39 | 66% | 20 | 34% |
| I feel more confident when I don't wear makeup | 58 | 36 | 62% | 22 | 38% |

Example 5

Photographs of individuals with certain skin conditions were taken before and after daily consumption of the beverage composition described in Example 3.

FIG. 1A shows an area of an individual's skin affected by eczema before consumption of the beverage composition. FIG. 1B shows the same area of skin after the individual had been taking a daily dose of the beverage composition described in Example 3 for 15 days. Reduced inflammation, improved hydration and healing of the skin were visible after this period.

Figure 2B:
FIG. 2B shows the same area of skin after the individual had been taking the beverage composition of the present invention for 15 days.

FIG. 2A shows an area of an individual's skin affected by psoriasis before consumption of the beverage composition. FIG. 2B shows the same area of skin after the individual had been taking a daily dose of the beverage composition described in Example 3 for 15 days. Reduced inflammation, improved hydration and healing of the skin were visible after this period. The skin also appeared less red, and scabbing and flaking of the skin had also been reduced.

FIG. 3A shows an area of an individual's skin affected by psoriasis before consumption of the beverage composition. FIG. 3B shows the same area of skin after the individual had been taking a daily dose of the beverage composition described in Example 3 for 15 days. Reduced inflammation and healing of the skin were visible after this period. The skin also appeared less red, and scabbing of the skin had also been reduced.

Figure 4B:
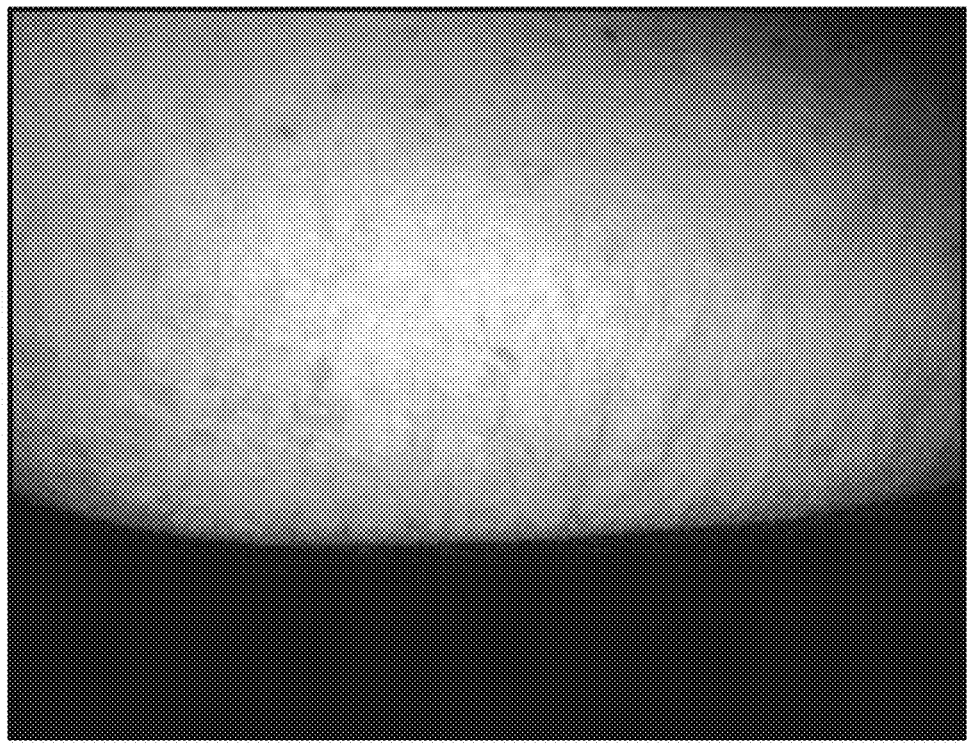
FIG. 4B shows the same area of skin after the individual had been taking the beverage composition of the present invention for 15 days.
Figure 4A:
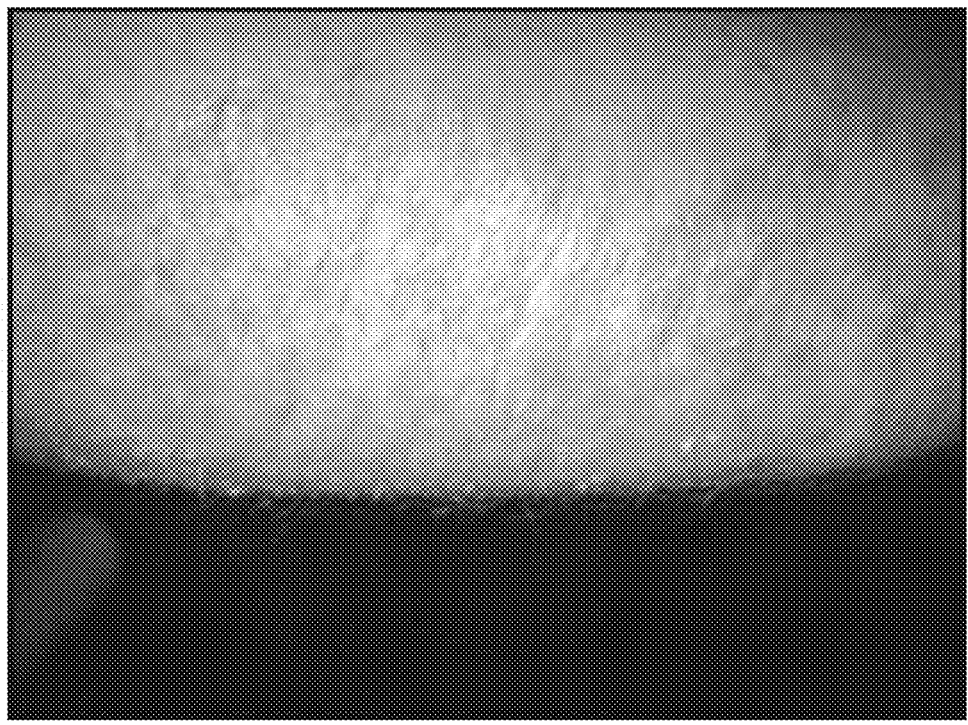
FIG. 4A shows an area of an individual's skin affected by psoriasis before consumption of the beverage composition of the present invention.

FIG. 4A shows an area of an individual's skin affected by psoriasis before consumption of the beverage composition.

FIG. 4B shows the same area of skin after the individual had been taking a daily dose of the beverage composition described in Example 3 for 15 days. Reduced inflammation and healing of the skin were visible after this period. The skin also appeared less red, less tight and more supple. A reduction in scarring of the tissue was also observed.

Figure 5A:
FIG. 5A shows an area of an individual's skin affected by acne before consumption of the beverage composition of the present invention.
Figure 5B:
FIG. 5B shows the same area of skin after the individual had been taking the beverage composition of the present invention for 8 weeks.

FIG. 5A shows an area of an individual's skin affected by acne before consumption of the beverage composition. FIG. 5B shows the same area of skin after the individual had been taking a daily dose of the beverage composition described in Example 3 for 8 weeks. Reduced inflammation and healing of the skin were visible after this period. The number of blocked and inflamed pores was also reduced.

FIG. 6A shows an area of an individual's skin affected by cellulite before consumption of the beverage composition. FIG. 6B shows the same area of skin after the individual had been taking a daily dose of the beverage composition described in Example 3 for 15 days. Improvements in the tightness and elasticity of the skin were observed after this period. The "orange-peel" appearance associated with the cellulite condition was reduced and the skin appeared to be smoother.

It should be understood that the present invention has been described only by way of example and that modifications of the composition may be made within the scope of the accompanying claims.

The invention claimed is:

1. A beverage composition comprising
about 7.0 g/150 ml of hydrolysed marine collagen;
about 180 mg/150 ml of calcium ascorbate;
about 1.0 g/150 ml of methyl sulphonyl methane;
about 4 mg/150 ml of vitamin B1;
about 6 mg/150 ml of vitamin B2;
about 17 mg/150 ml of vitamin B3;
about 21 mg/150 ml of vitamin B5;
about 4 mg/150 ml of vitamin B6;
about 200 μg/150 ml of vitamin B7;
about 200 μg/150 ml of vitamin B9;
about 10 μg/150 ml of vitamin B12;
about 124 mg/150 ml of L-lysine;
about 45 mg/150 ml of flax seed oil;
and wherein the beverage composition does not contain hyaluronic acid.

* * * * *